United States Patent
Liu et al.

(10) Patent No.: US 11,175,207 B2
(45) Date of Patent: Nov. 16, 2021

(54) METHOD FOR OBTAINING CONVERSION RELATIONSHIP BETWEEN DYNAMIC AND STATIC ELASTIC PARAMETERS

(71) Applicant: PetroChina Company Limited, Beijing (CN)

(72) Inventors: Zhonghua Liu, Beijing (CN); Lianteng Song, Beijing (CN); Haitao Zhang, Beijing (CN); Jixin Deng, Beijing (CN); Xia Li, Beijing (CN); Chao Yuan, Beijing (CN); Xiaoming Yang, Beijing (CN); Xiangzhi Cheng, Beijing (CN)

(73) Assignee: PetroChina Company Limited, Beijing (CN)

(*) Notice: Subject to any disclaimer, the term of this patent is extended or adjusted under 35 U.S.C. 154(b) by 612 days.

(21) Appl. No.: 16/062,309

(22) PCT Filed: Apr. 19, 2017

(86) PCT No.: PCT/CN2017/081030
§ 371 (c)(1),
(2) Date: Jun. 14, 2018

(87) PCT Pub. No.: WO2018/113149
PCT Pub. Date: Jun. 28, 2018

(65) Prior Publication Data
US 2019/0265142 A1 Aug. 29, 2019

(30) Foreign Application Priority Data
Dec. 20, 2016 (CN) .......................... 201611183911.8

(51) Int. Cl.
*G01N 3/40* (2006.01)
*G01N 23/20* (2018.01)
(Continued)

(52) U.S. Cl.
CPC .................. *G01N 3/40* (2013.01); *G01L 1/24* (2013.01); *G01N 23/20* (2013.01); *G01N 33/24* (2013.01);
(Continued)

(58) Field of Classification Search
CPC .......... G01N 3/40; G01N 23/20; G01N 33/24; G01L 1/24; G06F 17/10
See application file for complete search history.

(56) References Cited

U.S. PATENT DOCUMENTS

| | | | |
|---|---|---|---|
| 2011/0015907 A1* | 1/2011 | Crawford | G01V 99/00 703/2 |
| 2011/0246159 A1* | 10/2011 | Herwanger | G01V 1/306 703/7 |
| 2016/0069182 A1* | 3/2016 | Neale | E21B 47/16 166/254.2 |

FOREIGN PATENT DOCUMENTS

| | | |
|---|---|---|
| CN | 103257081 A | 8/2013 |
| CN | 103267678 A | 8/2013 |

(Continued)

OTHER PUBLICATIONS

Malgorzata, "Static and dynamic elastic properties, the cause of the difference and conversion methods—case study", 2015. (Year: 2015).*

(Continued)

*Primary Examiner* — Regis J Betsch
*Assistant Examiner* — Jeremy A Delozier
(74) *Attorney, Agent, or Firm* — Michael Best and Friedrich LLP

(57) ABSTRACT

A method for obtaining a conversion relationship between dynamic and static elastic parameters includes: Step S1, acquiring horizontal cores at different depths of the destination formation; Step S2, measuring the dynamic elastic parameters of the horizontal core under different pressures;

(Continued)

Step S3, measuring the static elastic parameters of the horizontal core under different pressures; Step S4, measuring the clay content of the horizontal core; Step S5 establishing a function relationship of the ratio between the dynamic and static elastic parameters with the formation pressure and clay content; and completing the conversion between the dynamic and static elastic parameters. The technical solution provided by the present invention takes full account of the influence of the formation stress and the clay content on the conversion rule of dynamic and static elastic parameters and is of great significance for improving the logging evaluation accuracy of rock mechanical parameters.

20 Claims, 6 Drawing Sheets

(51) Int. Cl.
G01N 33/24 (2006.01)
G01L 1/24 (2006.01)
G06F 17/10 (2006.01)
(52) U.S. Cl.
CPC ....... *G06F 17/10* (2013.01); *G01N 2223/616* (2013.01)

(56) References Cited

FOREIGN PATENT DOCUMENTS

| CN | 104267435 A | 1/2015 |
| CN | 104406849 A | 3/2015 |
| CN | 104853822 A | 8/2015 |
| CN | 104977618 A | 10/2015 |
| CN | 105370267 A | 3/2016 |
| CN | 105865955 A | 8/2016 |
| WO | WO-2014/205248 A3 | 12/2014 |

OTHER PUBLICATIONS

Brotons et al, "Improved correlation between the static and dynamic elastic modulus of different types of rocks", 2016. (Year: 2016).*
First Office Action dated May 22, 2019 for counterpart Australian patent application No. 2017363224 (9 pages).
Australian Patent Office Examination Report for Application No. 2017363224 dated Oct. 15, 2019 (4 pages).
Jiangping Liu et al., "*Test Research on Relativity between Dynamic and Static Elastic Modulus of Clay*", Chinese Journal of Rock Mechanics and Engineering, vol. 26, No. 2, pp. 427-431 (Feb. 2007).
Lixin Zeng, "*Variation and correlation of rock dynamic and static parameters in Songhua area of Baima*", Drilling and Production Technology, pp. 22-24 (2001).
International Search Report issued for counterpart Chinese Patent Application No. PCT/CN2016/099826 dated Dec. 22, 2016.
Australian Patent Office Examination Report for Application No. 2017363224 dated Jan. 23, 2020 (3 pages).
Chinese Patent Office Action and Search Report dated Dec. 21, 2018, for Application No. 201611183911.8 (13 pages, English translation included).
Hongkui et al., "Experimental Investigation on Poroelasticity of Sandstones," Chinese Journal of Rock Mechanics and Engineering, 2001, vol. 20, No. 3, pp. 332-337 (English abstract included).
Wang et al., "Progress of geophysical well logging in shale gas reservoir evaluation," Progress in Geophysics, 2015, vol. 30, No. 1, pp. 228-241 (English abstract included).
Zhu et al., "Study on correlation of dynamic and static springback modulus of subgrade in Shanxi Province," Journal ol China and Foreign Highway, 2016, vol. 36, No. 2, pp. 29-33 (statement of relevance included).

* cited by examiner

METHOD FOR OBTAINING CONVERSION RELATIONSHIP BETWEEN DYNAMIC AND STATIC ELASTIC PARAMETERS

CROSS REFERENCE TO RELATED APPLICATIONS

This application is a U.S. national phase application of PCT/CN2017/081030, filed Apr. 19, 2017, which claims priority to Chinese Patent Application No.: 2016111839118, filed Dec. 20, 2016, the entire contents of both of which are herein incorporated by reference.

FIELD OF THE INVENTION

The present invention relates to a method for obtaining a conversion relationship between dynamic and static elastic parameters and belongs to the art of petroleum exploration and logging.

BACKGROUND TO THE INVENTION

Dense reservoirs with low-permeability are becoming the focus and challenging field in oil and gas exploration. The establishment of a proper method for conversion between dynamic and static elastic parameters is of great significance for the accurate evaluation of the rock mechanical characteristics of formations by using logging data, and thereby optimizing fracturing testing well sections as well as optimizing oil testing completion solutions.

Elastic parameters are parameters that are used to describe the magnitude of the stress between the rock and the resulting strain, such as Young's modulus, Poisson's ratio and the like. There are two approaches to obtain elastic parameters: one is to obtain dynamic elastic parameters of rock through laboratory ultrasonic and density measurements or through acoustic and density logging data at continuous downhole depths; the other is to obtain static elastic parameters of rock through stress and strain measurements in laboratories. Static elastic parameters are significant guidance for oil and gas formation fracturing transformation, but cannot be continuously applied downhole since they can only be obtained through measurements in laboratories. Therefore, in general, dynamic elastic parameters at continuous depths are firstly obtained by using well logging data, which are then converted into static elastic parameters by using the conversion rule between dynamic elastic parameters and static elastic parameters obtained through experimental measurements, and the static elastic parameters are eventually applied in the evaluation of rock mechanical parameters of downhole full profile formation.

In the current techniques of conversion between dynamic and static elastic parameters, a series of plunger samples obtained from drilling and coring are placed in a laboratory, dynamic and static elastic parameters are measured under similar formation conditions, and a linear conversion relationship between the dynamic and static elastic parameters are then established. The obvious deficiency present in the prior art lies in that the influence of continuous changes of formation stress and lithology possibly occurring in the same geological layer on the conversion rule between dynamic and static elastic parameters is not taken into account. Therefore, based on the existing technology, it is difficult to accurately and continuously evaluate the rock mechanical parameters of formations with major heterogeneous changes, which limits the precise evaluation of reservoir completion qualities, thereby hampering the optimization of fracturing testing solutions and the realization of goals of cost reduction and efficiency improvement.

SUMMARY OF THE INVENTION

In order to solve the above technical problems, the present invention provides a method for obtaining a conversion relationship between dynamic and static elastic parameters, which takes full account of the influence of formation stress and clay content on the conversion rule between dynamic and static elastic parameters, and is significant for improving logging evaluation accuracy of rock mechanical parameters.

To achieve the above object, the present invention provides a method for obtaining a conversion relationship between dynamic and static elastic parameters, comprising the following steps:

Step S1, acquiring horizontal cores at different depths of the destination formation;

Step S2, measuring the dynamic elastic parameters of the horizontal cores under different pressures;

Step S3, measuring the static elastic parameters of the horizontal cores under different pressures;

Step S4, measuring the clay content of the horizontal cores;

Step S5, establishing a function relationship of the ratio between the dynamic and static elastic parameters with the formation pressure and clay content; and completing the conversion between the dynamic and static elastic parameters.

In the technical solution provided by the invention, the dynamic and the static elastic parameters as well as the clay contents of the horizontal cores are measured at different depths in the reservoir under different formation pressures, a functional relationship of the ratio between the dynamic and static elastic parameters with the formation pressures and clay contents is established on the basis of the measurement results, and a conversion rule between the dynamic and static elastic parameters is obtained. The technical solution provided by the present invention gives more accurate results due to full consideration of multiple influencing factors such as formation pressure and lithology changes.

In the above method, preferably, in step S1, the acquiring horizontal cores at different depths in the destination formation includes the following steps:

Step S101, m pieces of cores are obtained by drilling in the horizontal direction at the same formation depth D1, denoted as $D_{11}$, $D_{12}$, $D_{13}$, ..., and $D_{1m}$, respectively;

Step S102, each of the m pieces of cores drilled at the formation depth D1 is divided into two smaller pieces, denoted as $D_{11A}$, $D_{11B}$, $D_{12A}$, $D_{12B}$, $D_{13A}$, $D_{13B}$, ..., $D_{1mA}$, and $D_{1mB}$, respectively;

Step S103: following the operation of Step S101 and Step S102, m pieces of cores at the formation depth D2 are obtained by drilling, with each of the m pieces of cores at D2 being divided into two smaller pieces, denoted as $D_{21A}$, $D_{21B}$, $D_{22A}$, $D_{22B}$, $D_{23A}$, $D_{23B}$, ..., $D_{2mA}$, and $D_{2mB}$, respectively;

similarly, m pieces of cores at the formation depth Dn are obtained by drilling, with each of the m pieces of cores at Dn being divided into two smaller pieces, denoted as $D_{n1A}$, $D_{n1B}$, $D_{n2A}$, $D_{n2B}$, $D_{n3A}$, $D_{n3B}$, ..., $D_{nmA}$, and $D_{nmB}$, respectively.

In the above method, preferably, in step S101, the length of the core is at least 8 cm, preferably 8-10 cm; and the diameter is 2.5-5 cm, preferably 2.5 cm, but not limited thereto.

In the above method, preferably, in step S102, when each core is divided into two smaller pieces, the length of each core of the two smaller pieces is at least 4 cm, preferably 4 to 5 cm; the diameter is 2.5-5 cm, preferably 2.5 cm, but not limited thereto.

In the technical solution provided by the present invention, the depth interval, the number and the size of the horizontal cores can be appropriately configured according to practical survey needs and experimental accuracy requirements. In general, in order to ensure the accuracy of subsequent X-ray diffraction measurements and the requirements of measurements under multi-formation pressure conditions, the number and weight of the horizontal cores obtained need to meet certain requirements in design.

In the technical solution provided by the present invention, in step S1, $D_{11}$ represents a core obtained from the first step at the formation depth D1, $D_{12}$ represents a core obtained from the second step at the formation depth D1, ... $D_{1m}$ represents a core obtained from the $m^{th}$ step at the formation depth D1; $D_{nm}$ represents a core obtained from $m^{th}$ step at the formation depth Dn, and so on.

In the above method, preferably, in step S2, the measuring the dynamic elastic parameters of the horizontal core under different pressures includes the following steps:

Step S201, based on the pressure of the destination formation, m formation pressure values are set in an ascending order, denoted as P1, P2, P3, ..., and Pm, respectively; wherein the pressure interval [P1, Pm] includes the pressure of the entire destination formation, i.e., P1-Pm encompasses the pressures across the entire destination formation;

Step S202, under the pressure of P1, the horizontal cores $D_{11A}$, $D_{21A}$, $D_{31A}$, ..., and $D_{n1A}$ obtained from the first step at different formation depths are measured and the dynamic elastic parameters thereof are calculated and respectively denoted as $Ed_{11}$, $Ed_{21}$, $Ed_{31}$, ..., and $Ed_{11}$; under the pressure of P2, the horizontal cores $D_{12A}$, $D_{22A}$, $D_{32A}$, ..., and $D_{n2A}$ obtained from the second step at different formation depths are measured and the dynamic elastic parameters thereof are calculated and respectively denoted as $E_{d12}$, $E_{d22}$, $E_{d32}$, ..., and $E_{dn2}$; under the pressure of Pm, the horizontal cores $D_{1mA}$, $D_{2mA}$, $D_{3mA}$, ..., and $D_{nmA}$ obtained from the $m^{th}$ step at different formation depths are measured and the dynamic elastic parameters thereof are calculated and respectively denoted as $Ed_{1m}$, $Ed_{2m}$, $Ed_{3m}$, ..., and $Ed_{nm}$, and so forth.

In the above method, preferably, in step S202, the measured items include a density, a longitudinal wave velocity and a shear wave velocity; and for the measurement method for the longitudinal wave velocity and the shear wave velocity, reference is made to SY/T 6351-2012; more preferably, the condition for the measurement is saturated brine condition.

In the above method, the number m of the formation pressure values corresponds to the number m of the cores obtained by drilling in the horizontal direction. Preferably, both m and n have a value of ≥3.

In the above method, preferably, in step S3, the measuring the static elastic parameters of the horizontal cores under different pressures includes the following steps:

Step S301: referring to step S201, based on the pressure of the destination formation, m formation pressure values are set in an ascending order, denoted as P1, P2, P3, ..., and Pm respectively; wherein the pressure interval [P1, Pm] includes the pressure of the entire destination formation, i.e., P1-Pm encompasses the pressures across the entire destination formation;

Step S302, under the pressure of P1, the horizontal cores $D_{11B}$, $D_{21B}$, $D_{31B}$, ..., and $D_{n1B}$ obtained from the first step at different formation depths are measured and the static elastic parameters thereof are calculated and respectively denoted $Es_{11}$, $Es_{21}$, $Es_{31}$, ..., and $Es_{n1}$; under the pressure of P2, the horizontal cores $D_{12B}$, $D_{22B}$, $D_{32B}$, ..., and $D_{n2B}$ obtained from the second step at different formation depths are measured and the static elastic parameters thereof are calculated and respectively denoted as $Es_{12}$, $Es_{22}$, $Es_{32}$, ..., and $Es_{n2}$; under the pressure of Pm, the horizontal cores $D_{1mB}$, $D_{2mB}$, $D_{3mB}$, ..., and $D_{nmB}$ obtained from the $m^{th}$ step at different formation depths are measured and the static elastic parameters thereof are calculated and respectively denoted as $Es_{1m}$, $Es_{2m}$, $Es_{3m}$, ..., and $Es_{nm}$, and so forth.

In the above method, preferably, in step S302, the measured items include stress and strain, and the stress and strain are measured in accordance with GBT23561.9-2009; more preferably, the condition for the measurement is saturated brine condition.

In the above method, preferably, in step S4, the measuring the clay contents of the horizontal cores includes the following steps:

the divided samples of the horizontal cores $D_{11B}$, $D_{12B}$, $D_{13B}$, ..., and $D_{1mB}$ which have been measured for the static elastic parameters are collected and subjected to X-ray diffraction measurement to obtain the clay content Vcl1 at the formation depth D1; the divided samples of the horizontal cores $D_{21B}$, $D_{22B}$, $D_{23B}$, ..., and $D_{2mB}$ which have been measured for the static elastic parameters are collected and subjected to X-ray diffraction measurement to obtain the clay content Vcl2 at the formation depth D2; the divided samples of the horizontal cores $D_{n1B}$, $D_{n2B}$, $D_{n3B}$, ..., and $D_{nmB}$ which have been measured for the static elastic parameters are collected and subjected to X-ray diffraction measurement to obtain the clay content Vcln at the formation depth Dn2; and so forth. For the X-ray diffraction measurement method, reference is made to the industrial standard SY/T5163-2010.

In the above method, preferably, in step S5, the establishing a function relationship of the ratio between the dynamic and static elastic parameters with the formation pressure and clay content includes the following steps:

Step S501: the ratios between the dynamic and static elastic parameters of the core sample at the formation depth D1 under the m pressure values among P1-Pm are calculated, denoted as $E_{d11}/E_{s11}$, $E_{d12}/E_{s12}$, $E_{d13}/E_{s13}$, ..., and $E_{d1m}/E_{s1m}$, respectively; a curve of the ratio between the dynamic and static elastic parameters at the formation depth of D1 with the pressure is plotted, that is, a curve of the ratios between the dynamic and static elastic parameters $E_{d11}/E_{s11}$, $E_{d12}/E_{s12}$, $E_{d13}/E_{s13}$, ..., and $E_{d1m}/E_{s1m}$ with their corresponding pressure values P1, P2, P3, ..., and Pm is plotted, and the relationship therebetween can be obtained from the curve;

the ratio between the dynamic and static elastic parameters of the core sample at the formation depth D2 under the m pressure values among P1-Pm are calculated, denoted as $E_{d21}/E_{s21}$, $E_{d22}/E_{s22}$, $E_{d23}/E_{s23}$, ..., and $E_{d2m}/E_{s2m}$, respectively; a curve of the ratio between the dynamic and static elastic parameters at the formation depth of D2 with the pressure is plotted, and the relationship therebetween can be obtained from the curve;

similarly, the ratio between the dynamic and static elastic parameters of the core sample at the formation depth Dn under the m pressure values among P1-Pm are calculated, denoted as $E_{dn1}/E_{sn1}$, $E_{dn2}/E_{sn2}$, $E_{dn3}/E_{sn3}$, ..., and $E_{dnm}/E_{snm}$, respectively; a curve of the ratio between the dynamic and static elastic parameters at the formation depth of Dn with the pressure is plotted, and the relationship therebetween can be obtained from the curve;

Step S502, when the pressure value is P1, the ratios between the dynamic and static elastic parameters of the core sample at n formation depths among D1-Dn are calculated, denoted as $E_{d11}/E_{s11}$, $E_{d21}/E_{s21}$, $E_{d31}/E_{s31}$, ..., and $E_{dn1}/E_{sn1}$, respectively; according to the obtained clay contents Vcl1, Vcl2, Vcl3, ..., and Vcln at the n formation depths among D1-Dn, a curve of the ratio between the dynamic and static elastic parameters with the clay content at the pressure value of P1 is plotted, that is, a curve of the ratios $E_{d11}/E_{s11}$, $E_{d21}/E_{s21}$, $E_{d31}/E_{s31}$, ..., and $E_{dn1}/E_{sn1}$, with their corresponding clay contents Vcl1, Vcl2, Vcl3, ..., and Vcln is plotted, and the relationship therebetween can be obtained from the curve; when the pressure value is P2, the ratios between the dynamic and static elastic parameters of the core sample at n formation depths among D1-Dn are calculated, denoted as $E_{d12}/E_{s12}$, $E_{d22}/E_{s22}$, $E_{d32}/E_{s32}$, ..., and $E_{dn2}/E_{sn2}$, respectively; according to the obtained clay contents Vcl1, Vcl2, Vcl3, ..., and Vcln at the n formation depths among D1-Dn, a curve of the ratio between the dynamic and static elastic parameters with the clay content under the pressure value of P2 is plotted;

similarly, when the pressure value is Pm, the ratios between the dynamic and static elastic parameters of the core sample at n formation depths among D1-Dn are calculated, denoted as $E_{d1m}/E_{s1m}$, $E_{d2m}/E_{s2m}$, $E_{d3m}/E_{s3m}$, ..., and $E_{dnm}/E_{snm}$, respectively; according to the obtained clay contents Vcl1, Vcl2, Vcl3, ..., and Vcln at the n formation depths among D1-Dn, a curve of the ratio between the dynamic and static elastic parameters with the clay content under the pressure value of Pm is plotted;

Step S503: according to the relationship obtained in Step S501 and Step S502, a function relationship of the ratio between the dynamic and static elastic parameters with the formation pressure and clay content $E_d/E_s=f(P,Vcl)$ is established.

The advantageous effects of the present invention are as follows:

1) in the technical solution provided by the invention, the dynamic and the static elastic parameters and the clay contents of the horizontal cores at different depths in the reservoir under different formation pressures are measured, and a functional relationship of the ratio between the dynamic and static elastic parameters with the formation pressure and clay content is established on the basis of the measurements results, and a conversion rule between the dynamic and static elastic parameters are thus obtained; the technical solution provided by the present invention gives more accurate results due to full consideration of multiple influencing factors such as formation pressure and lithology changes;

2) in the technical solution provided by the present invention, the influence of the formation stress conditions and the clay content on the conversion rule between dynamic and static elastic parameters is taken into sufficient account, which is significant for improving the logging evaluation accuracy of rock mechanical parameters.

Figure 1:
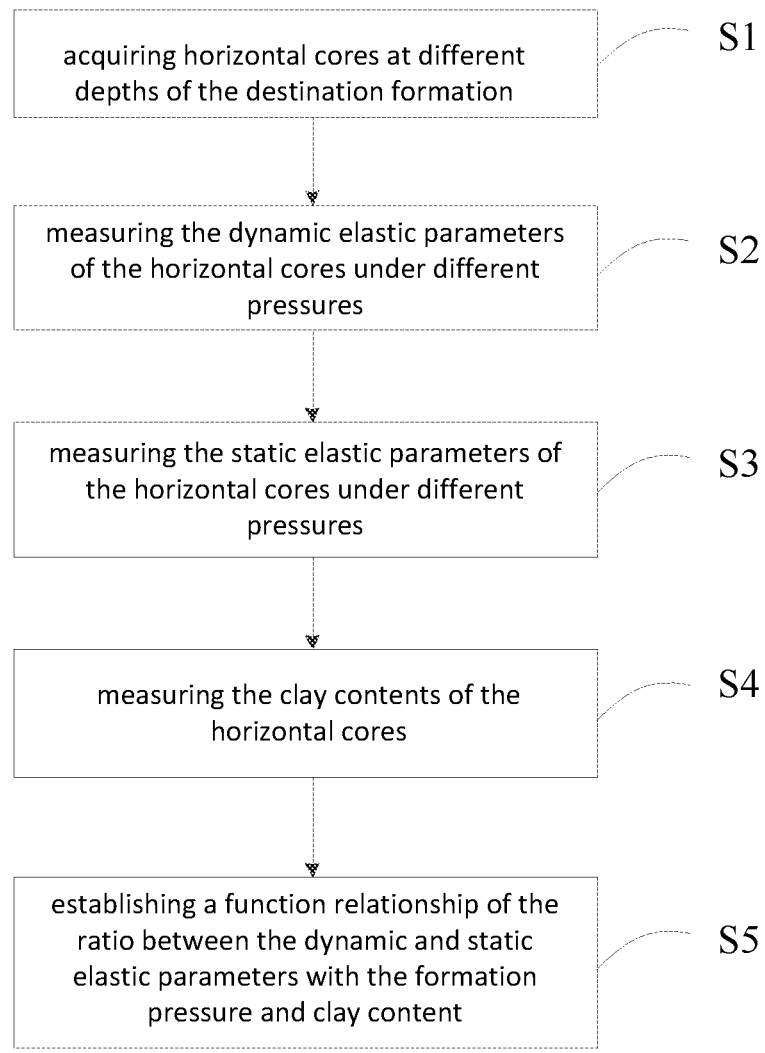
FIG. 1 is a schematic flow chart of a method for converting dynamic and static elastic parameters according to an example of the present invention.

DESCRIPTION OF THE KEY REFERENCE NUMBERS IN THE DRAWINGS 1. displacement meter; 2: first probe; 3: second probe; 4. measuring tube; 5. pore fluid control unit; 6: temperature control unit; 7: confining pressure control unit; 8: data acquisition and analysis unit.

DETAILED DESCRIPTION OF THE INVENTION

For better understanding of the technical features, objects and advantageous effects of the present invention, the technical solutions of the present invention are now described in details below, which cannot be construed as limiting to the scope of the embodiments of the present invention.

EXAMPLES

This example provides a method for obtaining a conversion relationship between dynamic and static elastic parameters (the flow of which is shown in FIG. 1), which includes the following steps:

Step S1, acquiring horizontal cores at different depths of the destination formation:

Horizontal plunger-like cores were obtained by drilling at different depths in the exploration area, with a set consisted of m=4 horizontal small cores obtained by drilling at the same formation depth; A total of n=8 sets of cores were obtained, denoted as $D_{11}$, $D_{12}$, $D_{13}$, $D_{14}$; $D_{21}$, $D_{22}$, $D_{23}$, $D_{24}$; ...; and $D_{81}$, $D_{82}$, $D_{83}$, $D_{84}$; wherein, each horizontal core was 2.5 cm in diameter and 8-10 cm in length.

The above cores were cut, respectively, with each divided into two smaller pieces and the cutting surface parallel to the bottom surface of the plunger-like core, and the location of cutting point must ensure that each of the two pieces after cutting was 4-5 cm in length; the cores satisfying such conditions after cutting were respectively denoted as $D_{11A}$, $D_{11B}$, $D_{12A}$, $D_{12B}$, ..., $D_{14A}$, $D_{14B}$; $D_{21A}$, $D_{21B}$, $D_{22A}$, $D_{22B}$, ..., $D_{24A}$, $D_{24B}$; ...; and $D_{81A}$, $D_{81B}$, $D_{82A}$, $D_{82B}$, ..., $D_{84A}$, $D_{84B}$; wherein, $D_{11A}$, $D_{11B}$ indicated that after $D_{11}$ was cut into two smaller pieces, one of them was denoted as $D_{11A}$, and the other $D_{11B}$, respectively; and so on.

Step S2, measuring the dynamic elastic parameters of the horizontal cores under different pressures:

Based on the formation pressure, four formation pressure values were set in an ascending order, denoted as P1, P2, P3, and P4 (unit: MPa), wherein, P1=20 MPa, P2=30 MPa, P3=40 MPa, and P4=60 MPa; the pressure range of 20 MPa-60 MPa encompassed the pressure across the entire exploration area.

Under the condition of a pressure of P1=20 MPa, the horizontal cores $D_{11A}$, $D_{21A}$, $D_{31A}$, ..., and $D_{81A}$ obtained in step S1 were subjected to density and longitudinal and shear wave velocity measurements under saturated brine conditions (for the longitudinal and transverse wave velocity measurements, reference was made to SY/T 6351-2012).

Figure 2:
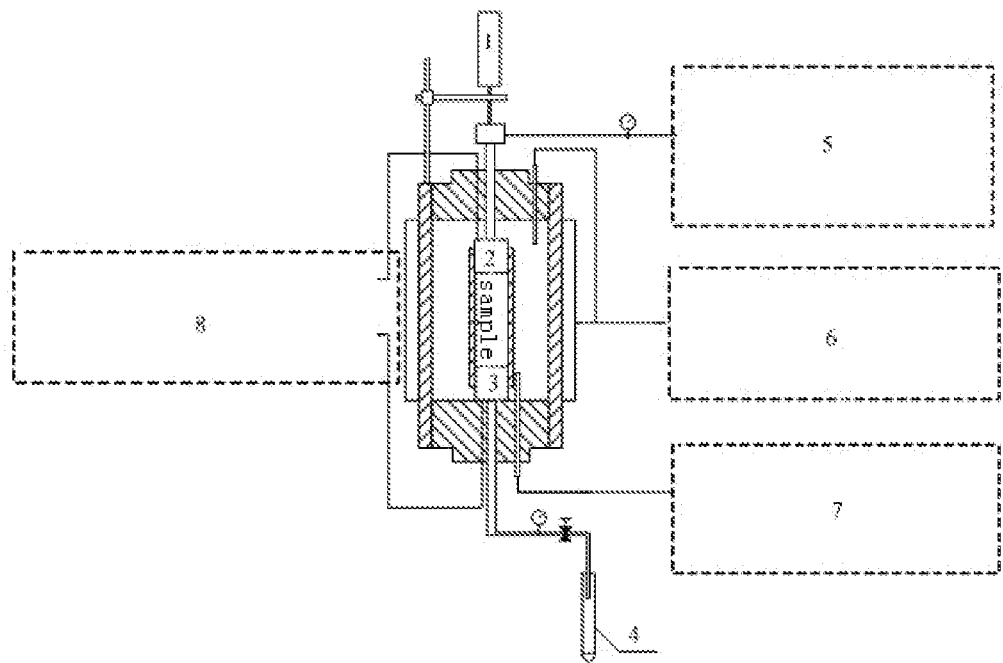
FIG. 2 is a schematic structural view of an apparatus for measuring the longitudinal and transverse wave velocities of a core according to an example of the present invention.

The device for measuring the longitudinal and shear wave velocities of the core was not particularly limited and could be a conventional measuring device in the art, such as the device shown in FIG. 2 (which was one of the conventional measurement devices in the art). The device included a displacement meter 1, a first probe 2, a second probe 3, a measuring tube 4, a pore fluid control unit 5, a temperature control unit 6, a confining pressure control unit 7, and a data acquisition and analysis unit 8. During the measurement, the measure conditions were regulated by the pore fluid control unit 5, the temperature control unit 6, and the confining pressure control unit 7. In this device, the displacement meter 1 could perform deformation measurement; the probes at both ends of the sample could allow the fluid passing through on one hand and allow energy being transmitted and received on the other hand, while the data resulted from the measurements could be sent to the data acquisition and analysis unit 8. This measuring device was only an exemplary device of the embodiment of the present invention. Other measuring devices having the same function or capable of fulfilling the same purpose could also be used for the measurement of the longitudinal and shear wave velocities of cores.

The measurement results are shown in Table 1, with their dynamic Young's moduli $Ed_{11}$, $Ed_{21}$, $Ed_{31}$, ..., and $Ed_{81}$ calculated; wherein, the dynamic Young's moduli were calculated with an equation as shown in Equation 1:

$$E = \frac{\rho V_s^2 (3V_p^2 - 4V_s^2)}{V_p^2 - V_s^2} \quad \text{Equation 1}$$

In Equation 1, E is dynamic Young's modulus, KPa; $\rho$ is density, g/cm³, $V_p$ is longitudinal wave velocity, m/s, $V_s$ is shear wave velocity, m/s,

TABLE 1

| Sample No. | Experimental confining pressure (MPa) | Density g/cm³ | Longitudinal wave velocity (m/s) | shear wave velocity (m/s) | Dynamic Young's modulus (GPa) |
|---|---|---|---|---|---|
| $D_{11A}$ | 20 | 2.65 | 5663 | 3426 | 75.35 |
| $D_{12A}$ | 30 | 2.65 | 5704 | 3456 | 76.59 |
| $D_{13A}$ | 40 | 2.65 | 5728 | 3472 | 77.29 |
| $D_{14A}$ | 60 | 2.65 | 5742 | 3484 | 77.76 |
| $D_{21A}$ | 20 | 2.64 | 5641 | 3400 | 74.14 |
| $D_{22A}$ | 30 | 2.64 | 5674 | 3418 | 74.96 |
| $D_{23A}$ | 40 | 2.64 | 5688 | 3430 | 75.43 |
| $D_{24A}$ | 60 | 2.64 | 5697 | 3437 | 75.72 |
| $D_{31A}$ | 20 | 2.61 | 5186 | 2905 | 56.01 |
| $D_{32A}$ | 30 | 2.61 | 5243 | 2954 | 57.74 |
| $D_{33A}$ | 40 | 2.61 | 5272 | 2980 | 58.66 |
| $D_{34A}$ | 60 | 2.61 | 5309 | 3009 | 59.71 |
| $D_{41A}$ | 20 | 2.56 | 5138 | 2914 | 54.91 |
| $D_{42A}$ | 30 | 2.56 | 5225 | 2977 | 57.16 |
| $D_{43A}$ | 40 | 2.56 | 5279 | 3014 | 58.53 |
| $D_{44A}$ | 60 | 2.56 | 5314 | 3041 | 59.49 |
| $D_{51A}$ | 20 | 2.57 | 5045 | 2885 | 53.78 |
| $D_{52A}$ | 30 | 2.57 | 5087 | 2912 | 54.75 |
| $D_{53A}$ | 40 | 2.57 | 5110 | 2926 | 55.27 |
| $D_{54A}$ | 60 | 2.57 | 5126 | 2934 | 55.59 |
| $D_{61A}$ | 20 | 2.54 | 5048 | 2970 | 55.36 |
| $D_{62A}$ | 30 | 2.54 | 5164 | 3051 | 58.24 |
| $D_{63A}$ | 40 | 2.54 | 5224 | 3092 | 59.75 |
| $D_{64A}$ | 60 | 2.54 | 5273 | 3125 | 60.98 |
| $D_{71A}$ | 20 | 2.54 | 5030 | 2977 | 55.39 |
| $D_{72A}$ | 30 | 2.54 | 5108 | 3042 | 57.59 |
| $D_{73A}$ | 40 | 2.54 | 5163 | 3086 | 59.12 |
| $D_{74A}$ | 60 | 2.54 | 5201 | 3111 | 60.05 |
| $D_{81A}$ | 20 | 2.48 | 4764 | 2653 | 44.53 |
| $D_{82A}$ | 30 | 2.48 | 4841 | 2718 | 46.53 |
| $D_{83A}$ | 40 | 2.48 | 4895 | 2757 | 47.79 |
| $D_{84A}$ | 60 | 2.48 | 4935 | 2782 | 48.63 |

Then, under the condition of the pressure of P2=30 MPa, the horizontal cores $D_{12A}$, $D_{22A}$, $D_{32A}$, ..., and $D_{82A}$ obtained in Step S1 were subjected to density and longitudinal and shear wave velocity measurements under saturated brine conditions, and their dynamic Young's moduli $Ed_{12}$, $Ed_{22}$, $Ed_{32}$, ..., and $Ed_{82}$ were calculated.

Similarly, under the condition of the pressure of P4=60 MPa, the horizontal cores $D_{14A}$, $D_{24A}$, $D_{34A}$, ..., and $D_{84A}$ obtained in the step S1 were subjected to density and longitudinal and shear wave velocity measurements under saturated brine conditions, and their dynamic Young's moduli $Ed_{14}$, $Ed_{24}$, $Ed_{34}$, ..., and $Ed_{84}$ were calculated.

Step S3, measuring the static elastic parameters of the horizontal cores under different pressures:

Under the condition of the pressure of P1=20 MPa, the horizontal cores $D_{11B}$, $D_{21B}$, $D_{31B}$, ..., and $D_{81B}$ obtained in Step S1 were subjected to stress and strain measurements under saturated saline conditions (for the stress and strain measurements, reference was made to GBT23561.9-2009), and their static Young's moduli were calculated according to the measurement results (as shown in Table 2); wherein the static Young's moduli were calculated with an equation as shown in Equation 2:

$$E = \frac{\sigma_{ab}}{\varepsilon_{ab}} \quad \text{Equation 2}$$

In Equation 2:

$\sigma_{ab}$—the stress difference between the end point and starting point of the straight line segment of the curve of stress vs. axial strain, in megapascals (MPa);

$\varepsilon_{ab}$—the strain difference between the end point and starting point of the straight line segment of the curve of stress vs. axial strain, in percentage.

Similarly, under the conditions of pressure P2=30, 40 and 60 MPa, the horizontal cores $D_{12B}$, $D_{22B}$, $D_{32B}$, ..., $D_{82B}$, ..., $D_{14B}$, $D_{24B}$, $D_{34B}$, ..., $D_{84B}$ were subjected to stress and strain measurements under saturated saline conditions, and their static Young's moduli were calculated.

TABLE 2

| Sample No. | Experimental confining pressure (MPa) | Stress difference $\sigma_{ab}$ (MPa) | Strain difference $\varepsilon_{ab}$ (%) | Static Young's modulus (GPa) |
|---|---|---|---|---|
| $D_{11B}$ | 20 | 106.1708 | 0.2095 | 50.6 |
| $D_{12B}$ | 30 | 104.3521 | 0.1904 | 54.9 |
| $D_{13B}$ | 40 | 157.5117 | 0.2544 | 61.8 |
| $D_{14B}$ | 60 | 141.2113 | 0.2132 | 66.2 |
| $D_{21B}$ | 20 | 134.5789 | 0.2666 | 50.5 |
| $D_{22B}$ | 30 | 119.5818 | 0.2121 | 56.3 |
| $D_{23B}$ | 40 | 163.8272 | 0.2579 | 63.6 |
| $D_{24B}$ | 60 | 227.4188 | 0.3252 | 70 |
| $D_{31B}$ | 20 | 99.0613 | 0.2811 | 35.3 |
| $D_{32B}$ | 30 | 80.4307 | 0.2162 | 37.2 |
| $D_{33B}$ | 40 | 112.8493 | 0.291 | 38.8 |
| $D_{34B}$ | 60 | 107.6294 | 0.263 | 40.9 |
| $D_{41B}$ | 20 | 63.0874 | 0.1874 | 33.7 |
| $D_{42B}$ | 30 | 68.5192 | 0.1944 | 35.3 |
| $D_{43B}$ | 40 | 83.4911 | 0.2185 | 38.2 |
| $D_{44B}$ | 60 | 97.2092 | 0.2513 | 38.7 |
| $D_{51B}$ | 20 | 91.0993 | 0.275 | 33.1 |
| $D_{52B}$ | 30 | 94.6616 | 0.279 | 33.9 |
| $D_{53B}$ | 40 | 121.111 | 0.347 | 34.9 |
| $D_{54B}$ | 60 | 128.4008 | 0.358 | 35.9 |
| $D_{61b}$ | 20 | 91.6754 | 0.2513 | 36.5 |
| $D_{62B}$ | 30 | 88.6596 | 0.2226 | 39.8 |
| $D_{63B}$ | 40 | 97.4503 | 0.2286 | 42.6 |
| $D_{64B}$ | 60 | 101.1177 | 0.2189 | 46.1 |
| $D_{71B}$ | 20 | 76.6523 | 0.2076 | 36.9 |
| $D_{72B}$ | 30 | 96.5619 | 0.2431 | 39.7 |
| $D_{73B}$ | 40 | 107.8026 | 0.238 | 45.3 |
| $D_{74B}$ | 60 | 108.8003 | 0.2155 | 50.5 |
| $D_{81B}$ | 20 | 51.78 | 0.1859 | 27.9 |
| $D_{82B}$ | 30 | 90.3 | 0.2986 | 30.2 |
| $D_{83B}$ | 40 | 141.08 | 0.441 | 32 |
| $D_{84B}$ | 60 | 187.13 | 0.6021 | 31.1 |

Step S4, measuring the clay contents of the horizontal cores;

The divided samples of the core $D_{11B}$, $D_{12B}$, ..., $D_{14B}$ after the stress and strain measurement were collected and subjected to X-ray diffraction measurement, and the obtained clay content values represented the clay contents at the formation depth D1;

Similarly, the divided samples of the horizontal cores at other formation depths after the stress and strain measurement were respectively collected and subjected to X-ray diffraction measurement, and the obtained clay content values represented the clay contents at the corresponding formation depths, as shown in Table 3.

TABLE 3

| Sample No. | Total clay content |
|---|---|
| D1 | 3.5 |
| D2 | 2 |
| D3 | 19.8 |
| D4 | 20.8 |
| D5 | 16.7 |
| D6 | 12.5 |
| D7 | 11.8 |
| D8 | 14.2 |

Figure 3:
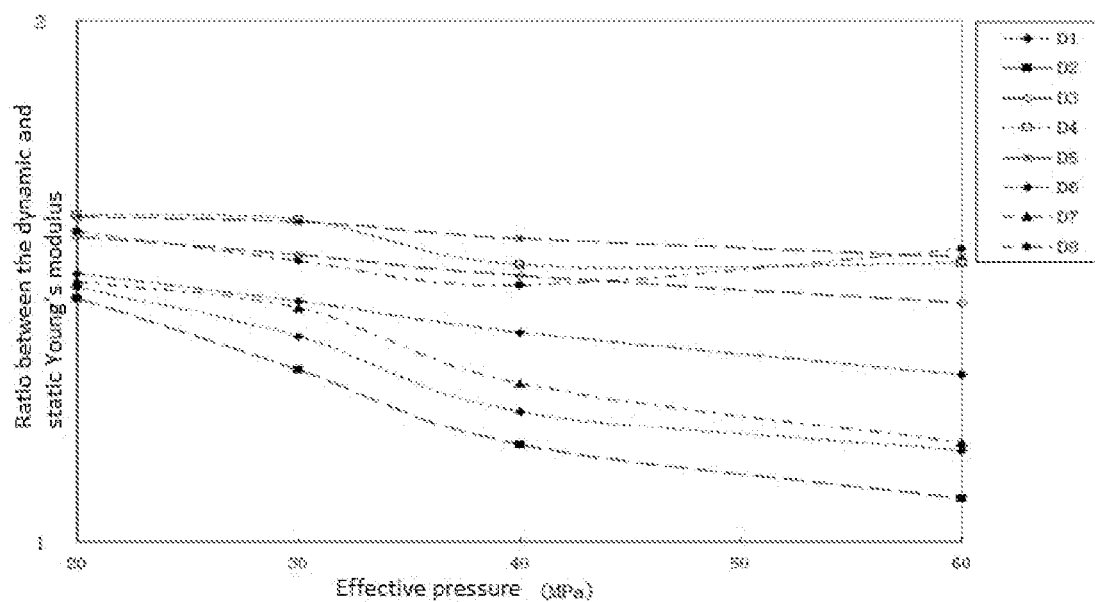
FIG. 3 is a graph of the relationship of the ratio between the dynamic and static elastic parameters with formation pressure according to an example of the present invention.
Figure 4:
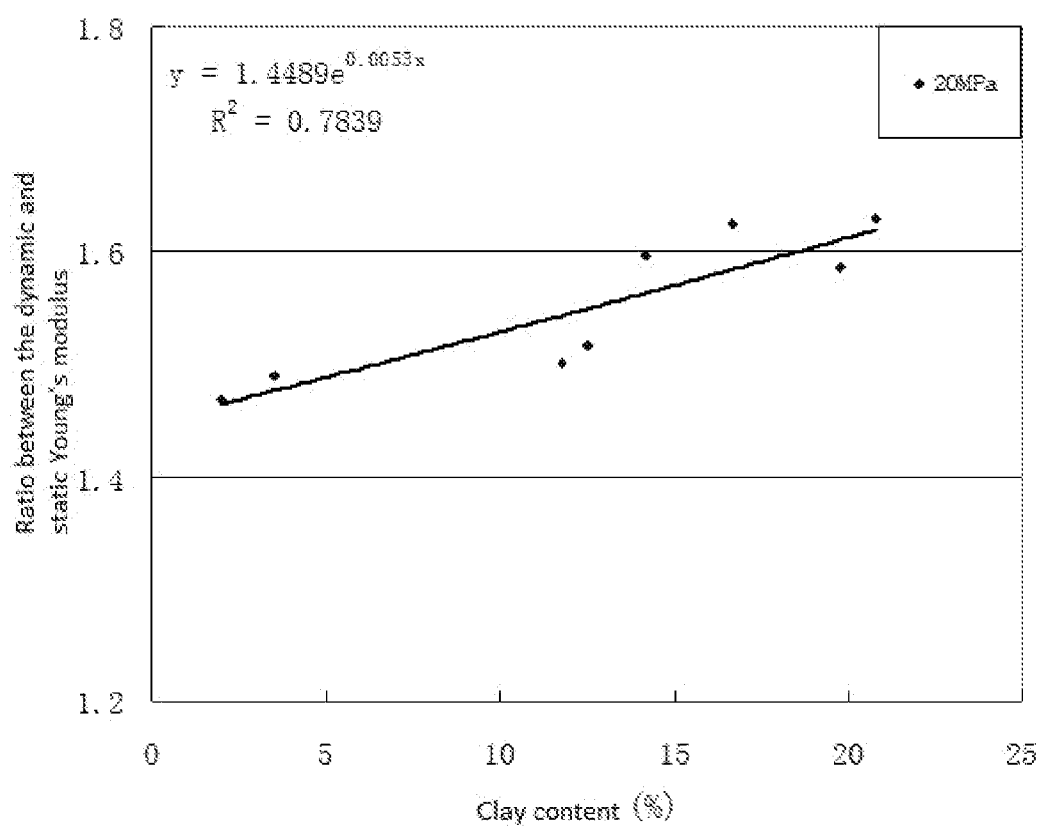
FIG. 4 is a graph of the relationship of the ratio between the dynamic and static elastic parameters with the clay content when the formation pressure is 20 Mpa according to an example of the present invention.
Figure 5:
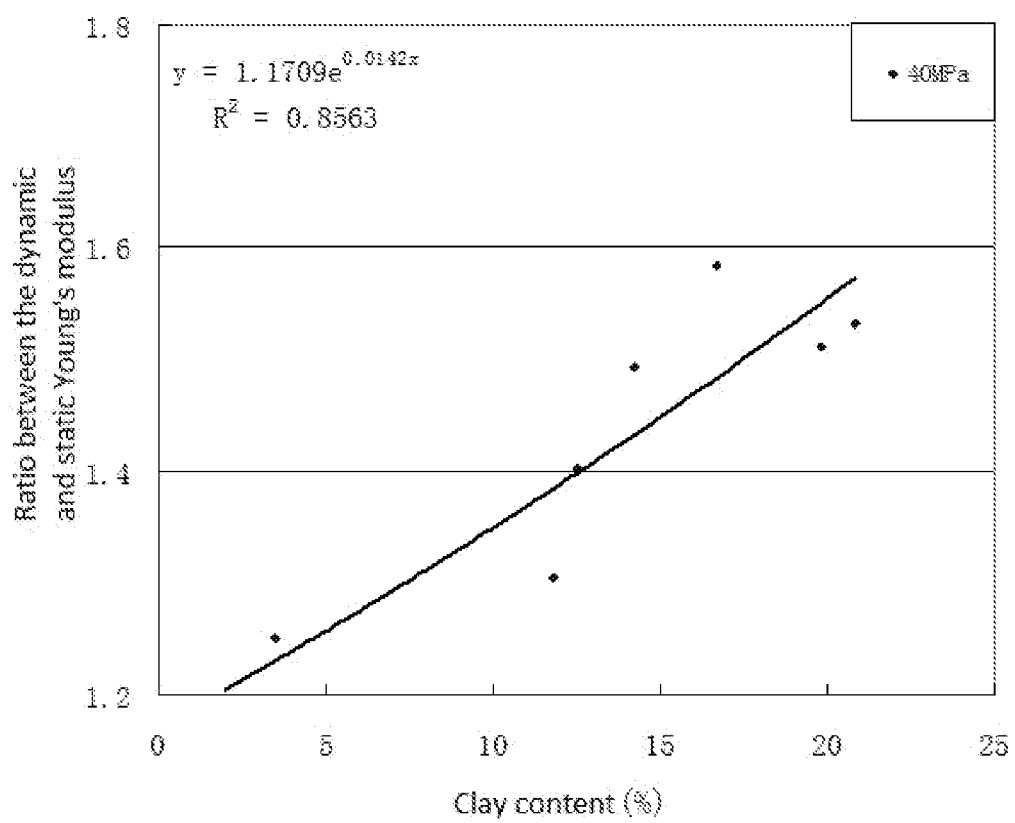
FIG. 5 is a graph of the relationship of the ratio between the dynamic and static elastic parameters with the clay content when the formation pressure is 40 Mpa according to an example of the present invention.

Step S5, establishing a function relationship of the ratio between the dynamic and static elastic parameters with the formation pressure and clay contents:

On the basis of the measured results at different formation depths under different pressure values, a relationship of the ratio between the dynamic and static elastic parameters (the ratio between the dynamic and static elastic parameters here referred to the ratio between the dynamic and static Young's modulus) with the formation pressure was established (as shown in FIG. 3). Meanwhile, a relationship of the ratio between the dynamic and static elastic parameters under a fixed pressure with the clay content was established in connection with the results of clay content measurements at various formation depths (as shown in FIG. 4 and FIG. 5 which demonstrated the relationship of the ratio between the dynamic and static elastic parameters and the clay content when the formation pressure was 20 MPa and 40 MPa respectively).

According to the relationship of the ratio between the dynamic and static elastic parameters with the formation pressure, together with the relationship thereof with the clay content under different formation pressures, a function relationship of the ratio between the dynamic and static elastic parameters with the clay content and formation pressure was established, as shown in Equation 2:

$$\frac{E_d}{E_s} = (A + B \cdot V_{clay}) \cdot P_{eff}^{C \cdot V_{clay} + D} \qquad \text{Equation 2}$$

In Equation 2, $E_d$ is dynamic elastic parameter (also referred to as dynamic Young's modulus), $E_s$ is static elastic parameter (also referred to as static Young's modulus), $V_{clay}$ is clay content, $P_{eff}$ is formation pressure, and A, B, C, and D are empirical coefficients obtained from experimental results. In this example, A=3.5, B=−8.14, C=1.35, and D=−0.3.

Figure 6:
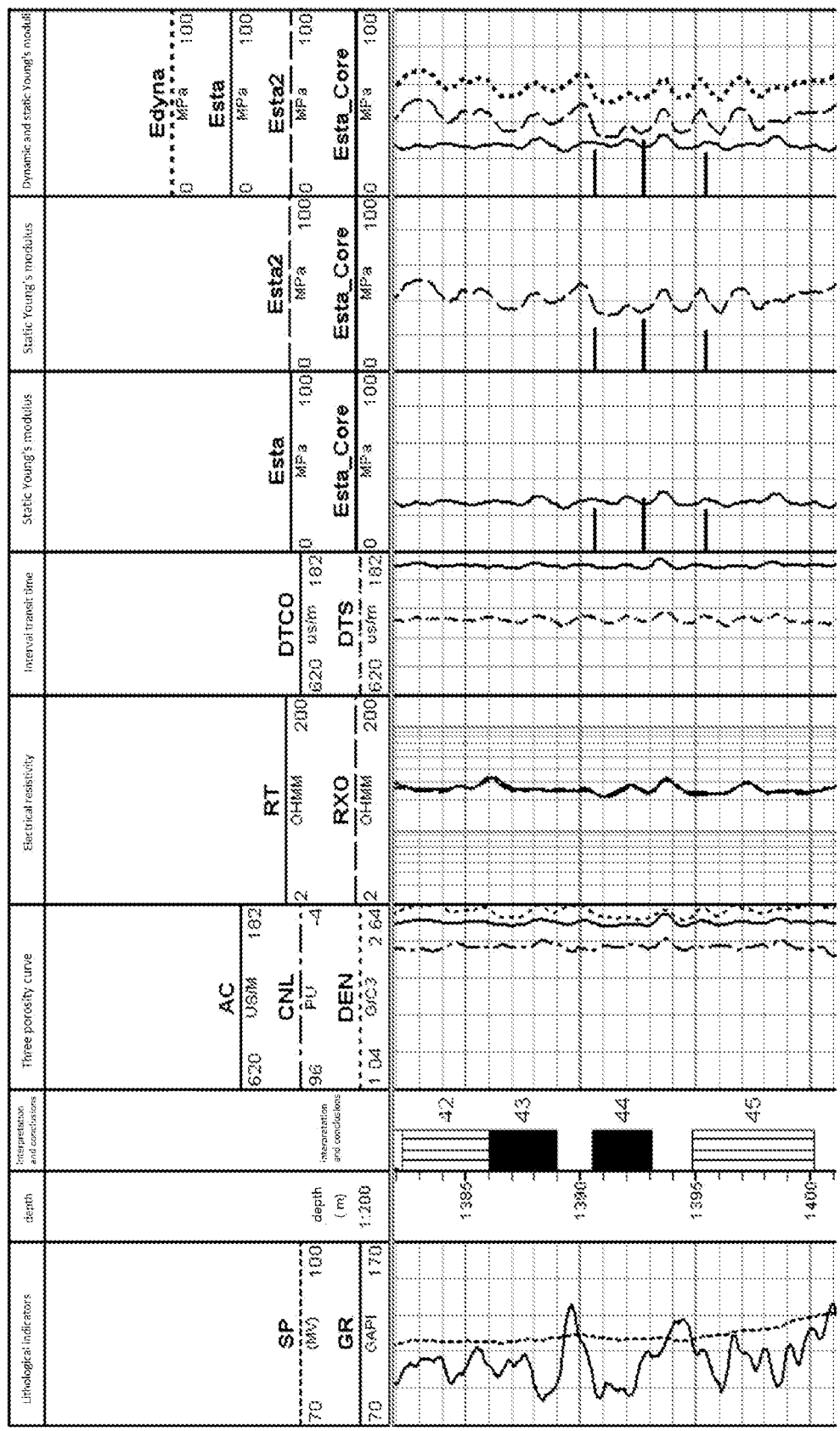
FIG. 6 is a comparison diagram of the practical effects according to an example of the present invention.

FIG. 6 is a comparison diagram of the effect of application in a well in the exploration area. Here, a total of 11 pieces of information was included, with Esta in the 9$^{th}$ representing the static Young's modulus calculated by the method provided in the example of the present invention, Esta2 representing the static Young's modulus calculated by a traditional dynamic and static linear regression method, and Esta_Core representing the static Young's modulus obtained from core measurements. The comparison results suggested that the results calculated by the method provided in the example of the present invention were closest to the results from the core measurements. The average relative error at three data points was 18%, as oppose to the average relative error from the conventional method of up to 45%. The statistical results from seven data points in three wells in the area demonstrated that the relative error of the method provided by the present invention was 13% in comparison with the results from the core measurements, as oppose to the relative error from the conventional method of up to 28%.

The foregoing describes only the preferred embodiments of the present invention, but is not intended to limit the present invention. Various modifications and changes can be made to the embodiments of the present invention for those skilled in the art. Any modifications, equivalent substitutions, improvements and the like made within the spirit and principle of the present invention are intended to be included in the protection scope of the present invention.

The invention claimed is:

1. A method for obtaining a conversion relationship between dynamic and static elastic parameters, comprising the following steps:
   Step S1, acquiring horizontal cores at different depths of the destination formation;
   Step S2, measuring with a device the dynamic elastic parameters of the horizontal cores under different effective formation stresses;

Step S3, measuring with a device the static elastic parameters of the horizontal cores under different effective formation stresses;

Step S4, measuring with a device the clay contents of the horizontal cores;

Step S5, establishing a function relationship of the ratio between the dynamic and static elastic parameters with the effective formation stress and clay content; and completing the conversion between the dynamic and static elastic parameters; and Step S6, using the function relationship to determine, with a control unit, rock mechanical parameters of the core.

2. The method according to claim 1, wherein in step S1, the acquiring horizontal cores at different depths in the destination formation includes the following steps:

Step S101, m pieces of cores are obtained by drilling in the horizontal direction at the same formation depth D1, denoted as $D_{11}$, $D_{12}$, $D_{13}$, . . . , and $D_{1m}$, respectively;

Step S102, each of the m pieces of cores drilled at the formation depth D1 is divided into two smaller pieces, denoted as $D_{11A}$, $D_{11B}$, $D_{12A}$, $D_{12B}$, $D_{13A}$, $D_{13B}$, . . . , $D_{1mA}$, and $D_{1mB}$, respectively;

Step S103: following the operation of Step S101 and Step S102, m pieces of cores at the formation depth Dn are obtained by drilling, with each of the m pieces of cores at Dn being divided into two smaller pieces, denoted as $D_{n1A}$, $D_{n1B}$, $D_{n2A}$, $D_{n2B}$, $D_{n3A}$, $D_{n3B}$, . . . , $D_{nmA}$, and $D_{nmB}$, respectively.

3. The method according to claim 2, wherein in step S101, the core is at least 8 cm in length and 2.5-5 cm in diameter.

4. The method according to claim 2, wherein in step S102, when each core is divided into two smaller pieces, each core of the two smaller pieces is at least 4 cm in length and 2.5-5 cm in diameter.

5. The method according to claim 2, wherein in step S2, the measuring the dynamic elastic parameters of the horizontal cores under different effective formation stresses includes the following steps:

Step S201, based on the pressure of the destination formation, m effective formation stress values are set in an ascending order, denoted as P1, P2, P3, . . . , and Pm, respectively; wherein the effective formation stress interval [P1, Pm] includes the pressure of the entire destination formation;

Step S202, under the effective formation stress of P1, the obtained horizontal cores $D_{11A}$, $D_{21A}$, $D_{31A}$, $D_{n1A}$ are measured and the dynamic elastic parameters thereof are calculated and respectively denoted as $Ed_{11}$, $Ed_{21}$, $Ed_{31}$, . . . , and $Ed_{n1}$;

following the above operation, the obtained horizontal cores $D_{1mA}$, $D_{2mA}$, $D_{3mA}$, . . . , $D_{nmA}$ are measured and the dynamic elastic parameters thereof are calculated and respectively denoted as $Ed_{1m}$, $Ed_{2m}$, $Ed_{3m}$, . . . , and $Ed_{nm}$.

6. The method according to claim 5, wherein in Step 202, the measured items include a density, a longitudinal wave velocity and a shear wave velocity.

7. The method according to claim 5, wherein in Step S3, the measuring the static elastic parameters of the horizontal core under different effective formation stresses includes the following steps:

Step S301: based on the pressure of the destination formation, m effective formation stress values are set in an ascending order, denoted as P1, P2, P3, . . . , Pm respectively; wherein the effective formation stress interval [P1, Pm] includes the effective formation stress of the entire destination formation;

Step S302, under the effective formation stress of P1, the obtained horizontal cores $D_{11B}$, $D_{21B}$, $D_{31B}$, $D_{n1B}$ are measured and the static elastic parameters thereof are calculated and respectively denoted as $Es_{11}$, $Es_{21}$, $Es_{31}$, . . . , and $Es_{n1}$;

following the above operation, under the effective formation stress of Pm, the obtained horizontal cores $D_{1mB}$, $D_{2mB}$, $D_{3mB}$, $D_{nmB}$ are measured and the static elastic parameters thereof are calculated and respectively denoted as $Es_{1m}$, $Es_{2m}$, $Es_{3m}$, . . . , and $Es_{nm}$.

8. The method according to claim 7, wherein in Step S302, the measured items include stress and strain.

9. The method according to claim 8, wherein, in Step S4, the measuring the clay content of the horizontal core includes the following steps:

Step S401, the horizontal cores $D_{11B}$, $D_{12B}$, $D_{13B}$, . . . , and $D_{1mB}$ which have been measured for the static elastic parameters are subjected to X-ray diffraction measurement to obtain the clay content Vcl1 at the formation depth D1;

Step S402, following the operation of Step S401, the horizontal cores $D_{n1B}$, $D_{n2B}$, $D_{n3B}$, . . . , and $D_{nmB}$ which have been measured for the static elastic parameters are subjected to X-ray diffraction measurement to obtain the clay content Vcln at the formation depth Dn.

10. The method according to claim 8, wherein, in Step S5, the establishing a function relationship of the ratio between the dynamic and static elastic parameters with the effective formation stress and clay content includes the following steps:

Step S501: the ratios between the dynamic and static elastic parameters of the core sample at the formation depth D1 under the m effective formation stress values among P1-Pm are calculated, denoted as $E_{d11}/E_{s11}$, $E_{d12}/E_{s12}$, $E_{d13}/E_{s13}$, . . . , and $E_{d1m}/E_{s1m}$, respectively; a relationship of the ratio between the dynamic and static elastic parameters at the formation depth of D1 with the effective formation stress is formulated;

following the above operation, the ratios between the dynamic and static elastic parameters of the core sample at the formation depth Dn under the m effective formation stress values among P1-Pm are calculated, denoted as $E_{dn1}/E_{sn1}$, $E_{dn2}/E_{sn2}$, $E_{dn3}/E_{sn3}$, . . . , and $E_{dnm}/E_{snm}$, respectively; a relationship of the ratio between the dynamic and static elastic parameters at the formation depth of Dn with the effective formation stress is formulated;

Step S502, when the effective formation stress value is P1, the ratios between the dynamic and static elastic parameters of the core sample at the n formation depths among D1-Dn are calculated, denoted as $E_{d11}/E_{s11}$, $E_{d21}/E_{s21}$, $E_{d31}/E_{s31}$, . . . , and $E_{dn1}/E_{sn1}$, respectively; according to the obtained clay contents Vcl1, Vcl2, Vcl3, . . . , and Vcln at the n formation depths among D1-Dn, a relationship of the ratio between the dynamic and static elastic parameters with the clay content under the effective formation stress value of P1 is formulated;

following the above operation, when the effective formation stress value is Pm, the ratios between the dynamic and static elastic parameters of the core sample at the n formation depths among D1-Dn are calculated, denoted as $E_{d1m}/E_{s1m}$, $E_{d2m}/E_{s2m}$, $E_{d3m}/E_{s3m}$, . . . , and $E_{dnm}/E_{snm}$, respectively; according to the obtained clay contents Vcl1, Vcl2, Vcl3, . . . , and Vcln at the n formation depths among D1-Dn, a relationship of the ratio between the dynamic and static elastic parameters with the clay content under the effective formation stress value of Pm is formulated;

Step S503: according to the relationships obtained in step S501 and step S502, a function relationship of the ratio between the dynamic and static elastic parameters with the effective formation stress and clay content $E_d/E_s=f(P,Vcl)$ is established.

11. The method according to claim 5, wherein in Step S302, the measured items include stress and strain.

12. The method according to claim 5, wherein, in Step S4, the measuring the clay content of the horizontal core includes the following steps:

Step S401, the horizontal cores $D_{11B}$, $D_{12B}$, $D_{13B}$, ..., and $D_{1mB}$ which have been measured for the static elastic parameters are subjected to X-ray diffraction measurement to obtain the clay content Vcl1 at the formation depth D1;

Step S402, following the operation of Step S401, the horizontal cores $D_{n1B}$, $D_{n2B}$, $D_{n3B}$, ..., and $D_{nmB}$ which have been measured for the static elastic parameters are subjected to X-ray diffraction measurement to obtain the clay content Vcln at the formation depth Dn.

13. The method according to claim 5, wherein, in Step S5, the establishing a function relationship of the ratio between the dynamic and static elastic parameters with the effective formation stress and clay content includes the following steps:

Step S501: the ratios between the dynamic and static elastic parameters of the core sample at the formation depth D1 under the m effective formation stress values among P1-Pm are calculated, denoted as $E_{d11}/E_{s11}$, $E_{d12}/E_{s12}$, $E_{d13}/E_{s13}$, ..., and $E_{d1m}/E_{s1m}$, respectively; a relationship of the ratio between the dynamic and static elastic parameters at the formation depth of D1 with the effective formation stress is formulated;

following the above operation, the ratios between the dynamic and static elastic parameters of the core sample at the formation depth Dn under the m effective formation stress values among P1-Pm are calculated, denoted as $E_{dn1}/E_{sn1}$, $E_{dn2}/E_{sn2}$, $E_{dn3}/E_{sn3}$, ..., $E_{dnm}/E_{snm}$, respectively; a relationship of the ratio between the dynamic and static elastic parameters at the formation depth of Dn with the effective formation stress is formulated;

Step S502, when the effective formation stress value is P1, the ratios between the dynamic and static elastic parameters of the core sample at the n formation depths among D1-Dn are calculated, denoted as $E_{d11}/E_{s11}$, $E_{d21}/E_{s21}$, $E_{d31}/E_{s31}$, ..., and $E_{dn1}/E_{sn1}$, respectively; according to the obtained clay contents Vcl1, Vcl2, Vcl3, ..., and Vcln at the n formation depths among D1-Dn, a relationship of the ratio between the dynamic and static elastic parameters with the clay content under the effective formation stress value of P1 is formulated; following the above operation, when the effective formation stress value is Pm, the ratios between the dynamic and static elastic parameters of the core sample at the n formation depths among D1-Dn are calculated, denoted as $E_{d1m}/E_{s1m}$, $E_{d2m}/E_{s2m}$, $E_{d3m}/E_{s3m}$, ..., and $E_{dnm}/E_{snm}$, respectively; according to the obtained clay contents Vcl1, Vcl2, Vcl3, ..., and Vcln at the n formation depths among D1-Dn, a relationship of the ratio between the dynamic and static elastic parameters with the clay content under the effective formation stress value of Pm is formulated;

Step S503: according to the relationships obtained in Step S501 and Step S502, a function relationship of the ratio between the dynamic and static elastic parameters with the effective formation stress and clay content $E_d/E_s=f(P,Vcl)$ is established.

14. The method according to claim 2, wherein in Step S3, the measuring the static elastic parameters of the horizontal cores under different effective formation stresses includes the following steps:

Step S301: based on the pressure of the destination formation, m effective formation stress values are set in an ascending order, denoted as P1, P2, P3, ..., and Pm respectively; wherein the effective formation stress interval [P1, Pm] includes the effective formation stress of the entire destination formation;

Step S302, under the effective formation stress of P1, the obtained horizontal cores $D_{11B}$, $D_{21B}$, $D_{31B}$, ... $D_{n1B}$ are measured and the static elastic parameters thereof are calculated and respectively denoted as $Es_{11}$, $Es_{21}$, $Es_{31}$, ..., and $Es_{n1}$;

following the above operation, under the effective formation stress of Pm, the obtained horizontal cores $D_{1mB}$, $D_{2mB}$, $D_{3mB}$, $D_{nmB}$ are measured and the static elastic parameters thereof are calculated and respectively denoted as $Es_{1m}$, $Es_{2m}$, $Es_{3m}$, ..., and $Es_{nm}$.

15. The method according to claim 14, wherein in Step S302, the measured items include stress and strain.

16. The method according to claim 14, wherein, in Step S4, the measuring the clay content of the horizontal core includes the following steps:

Step S401, the horizontal cores $D_{11B}$, $D_{12B}$, $D_{13B}$, ..., and $D_{1mB}$ which have been measured for the static elastic parameters are subjected to X-ray diffraction measurement to obtain the clay content Vcl1 at the formation depth D1;

Step S402, following the operation of Step S401, the horizontal cores $D_{n1B}$, $D_{n2B}$, $D_{n3B}$, ..., and $D_{nmB}$ which have been measured for the static elastic parameters are subjected to X-ray diffraction measurement to obtain the clay content Vcln at the formation depth Dn.

17. The method according to claim 14, wherein, in Step S5, the establishing a function relationship of the ratio between the dynamic and static elastic parameters with the effective formation stress and clay content includes the following steps:

Step S501: the ratio between the dynamic and static elastic parameters of the core sample at the formation depth D1 under the m effective formation stress values among P1-Pm is calculated, denoted as $E_{d11}/E_{s11}$, $E_{d12}/E_{s12}$, $E_{d13}/E_{s13}$, ..., and $E_{d1m}/E_{s1m}$, respectively; a relationship of the ratio between the dynamic and static elastic parameters at the formation depth of D1 with the effective formation stress is formulated;

Following the above operation, the ratio between the dynamic and static elastic parameters of the core sample at the formation depth Dn under the m effective formation stress values among P1-Pm is calculated, denoted as $E_{dn1}/E_{sn1}$, $E_{dn2}/E_{sn2}$, $E_{dn3}/E_{sn3}$, ..., $E_{dnm}/E_{snm}$, respectively; a relationship of the ratio between the dynamic and static elastic parameters at the formation depth of Dn with the effective formation stress is formulated;

Step S502, when the effective formation stress value is P1, the ratio between the dynamic and static elastic parameters of the core sample at n formation depths in D1-Dn is calculated, denoted as, $E_{d11}/E_{s11}$, $E_{d21}/E_{s21}$, $E_{d31}/E_{s31}$, ..., and $E_{dn1}/E_{sn1}$ respectively; according to the obtained clay contents Vcl1, Vcl2, Vcl3, ..., and Vcln of the n formation depths in D1-Dn, a relationship of the ratio between the dynamic and static elastic parameters with the clay content at the effective formation stress value of P1 is formulated;

Following the above operation, when the effective formation stress value is Pm, the ratio between the dynamic and static elastic parameters of the core sample at n formation depths in D1-Dn is calculated, denoted as, $E_{d1m}/E_{s1m}$, $E_{d2m}/E_{s2m}$, $E_{d3m}/E_{s3m}$, ..., and $E_{dnm}/E_{snm}$, respectively; according to the obtained clay contents Vcl1, Vcl2, Vcl3, ..., and Vcln of the n formation depths in D1-Dn, a relationship of the ratio between the dynamic and static elastic parameters with the clay content at the effective formation stress value of Pm is formulated;

Step S503: according to the relationship obtained in step S501 and step S502, a function relationship of the ratio between the dynamic and static elastic parameters with the effective formation stress and clay content $E_d/E_s=f$ (P,Vcl) is established.

18. The method according to claim 2, wherein in Step S4, the measuring the clay contents of the horizontal cores includes the following steps:

Step S401, the horizontal cores $D_{11B}$, $D_{12B}$, $D_{13B}$, ..., and $D_{1mB}$ which have been measured for the static elastic parameters are subjected to X-ray diffraction measurement to obtain the clay content Vcl1 at the formation depth D1;

Step S402, following the operation of Step S401, the horizontal cores $D_{n1B}$, $D_{n2B}$, $D_{n3B}$, ..., and $D_{nmB}$ which have been measured for the static elastic parameters are subjected to X-ray diffraction measurement to obtain the clay content Vcln at the formation depth Dn.

19. The method according to claim 18, wherein, in Step S5, the establishing a function relationship of the ratio between the dynamic and static elastic parameters with the effective formation stress and clay content includes the following steps:

Step S501: the ratios between the dynamic and static elastic parameters of the core sample at the formation depth D1 under the m effective formation stress values among P1-Pm are calculated, denoted as $E_{d11}/E_{s11}$, $E_{d12}/E_{s12}$, $E_{d13}/E_{s13}$, ..., and $E_{d1m}/E_{s1m}$, respectively; a relationship of the ratio between the dynamic and static elastic parameters at the formation depth of D1 with the effective formation stress is formulated;

following the above operation, the ratios between the dynamic and static elastic parameters of the core sample at the formation depth Dn under the m effective formation stress values among P1-Pm are calculated, denoted as $E_{dn1}/E_{sn1}$, $E_{dn2}/E_{sn2}$, $E_{dn3}/E_{sn3}$, ..., $E_{dnm}/E_{snm}$, respectively; a relationship of the ratio between the dynamic and static elastic parameters at the formation depth of Dn with the effective formation stress is formulated;

Step S502, when the effective formation stress value is P1, the ratios between the dynamic and static elastic parameters of the core sample at the n formation depths among D1-Dn are calculated, denoted as $E_{d11}/E_{s11}$, $E_{d21}/E_{s21}$, $E_{d31}/E_{s31}$, ..., and $E_{dn1}/E_{sn1}$, respectively; according to the obtained clay contents Vcl1, Vcl2, Vcl3, ..., and Vcln at the n formation depths among D1-Dn, a relationship of the ratio between the dynamic and static elastic parameters with the clay content under the effective formation stress value of P1 is formulated;

following the above operation, when the effective formation stress value is Pm, the ratios between the dynamic and static elastic parameters of the core sample at the n formation depths among D1-Dn are calculated, denoted as $E_{d1m}/E_{s1m}$, $E_{d2m}/E_{s2m}$, $E_{d3m}/E_{s3m}$, ..., and $E_{dnm}/E_{snm}$, respectively; according to the obtained clay contents Vcl1, Vcl2, Vcl3, ..., and Vcln at the n formation depths among D1-Dn, a relationship of the ratio between the dynamic and static elastic parameters with the clay content under the effective formation stress value of Pm is formulated;

Step S503: according to the relationships obtained in step S501 and step S502, a function relationship of the ratio between the dynamic and static elastic parameters with the effective formation stress and clay content $E_d/E_s=f$ (P,Vcl) is established.

20. The method according to claim 2, wherein, in Step S5, the establishing a function relationship of the ratio between the dynamic and static elastic parameters with the effective formation stress and clay content includes the following steps:

Step S501: the ratios between the dynamic and static elastic parameters of the core sample at the formation depth D1 under the m effective formation stress values among P1-Pm are calculated, denoted as $E_{d11}/E_{s11}$, $E_{d12}/E_{s12}$, $E_{d13}/E_{s13}$, ..., and $E_{d1m}/E_{s1m}$, respectively; a relationship of the ratio between the dynamic and static elastic parameters at the formation depth of D1 with the effective formation stress is formulated;

following the above operation, the ratios between the dynamic and static elastic parameters of the core sample at the formation depth Dn under the m effective formation stress values among P1-Pm are calculated, denoted as $E_{dn1}/E_{sn1}$, $E_{dn2}/E_{sn2}$, $E_{dn3}/E_{sn3}$, ..., and $E_{dnm}/E_{snm}$, respectively; a relationship of the ratio between the dynamic and static elastic parameters at the formation depth of Dn with the effective formation stress is formulated;

Step S502, when the effective formation stress value is P1, the ratios between the dynamic and static elastic parameters of the core sample at the n formation depths among D1-Dn are calculated, denoted as $E_{d11}/E_{s11}$, $E_{d21}/E_{s21}$, $E_{d31}/E_{s31}$, ..., and $E_{dn1}/E_{sn1}$, respectively; according to the obtained clay contents Vcl1, Vcl2, Vcl3, ..., and Vcln at the n formation depths among D1-Dn, a relationship of the ratio between the dynamic and static elastic parameters with the clay content under the effective formation stress value of P1 is formulated;

following the above operation, when the effective formation stress value is Pm, the ratios between the dynamic and static elastic parameters of the core sample at the n formation depths among D1-Dn are calculated, denoted as $E_{d1m}/E_{s1m}$, $E_{d2m}/E_{s2m}$, $E_{d3m}/E_{s3m}$, ..., and $E_{dnm}/E_{snm}$, respectively; according to the obtained clay contents Vcl1, Vcl2, Vcl3, ..., and Vcln at the n formation depths among D1-Dn, a relationship of the ratio between the dynamic and static elastic parameters with the clay content under the effective formation stress value of Pm is formulated;

Step S503: according to the relationships obtained in Step S501 and Step S502, a function relationship of the ratio between the dynamic and static elastic parameters with the effective formation stress and clay content $E_d/E_s=f(P,Vcl)$ is established.

\* \* \* \* \*